(12) United States Patent
Zeng et al.

(10) Patent No.: US 8,655,033 B2
(45) Date of Patent: Feb. 18, 2014

(54) ITERATIVE RECONSTRUCTION

(75) Inventors: Kai Zeng, Niskayuna, NY (US);
Charles Addison Bouman, Jr., West Lafayette, IN (US); Bruno Kristiaan Bernard De Man, Clifton Park, NY (US); Jiang Hsieh, Brookfield, WI (US); Ken David Sauer, South Bend, IN (US); Jean-Baptiste Daniel Marie Thibault, Milwaukee, WI (US); Zhou Yu, Minhang (CN)

(73) Assignees: General Electric Company, Schenectady, NY (US); University of Notre Dame Du Lac, Notre Dame, IN (US); Purdue Research Foundation, West Lafayette, IN (US)

( * ) Notice: Subject to any disclaimer, the term of this patent is extended or adjusted under 35 U.S.C. 154(b) by 1096 days.

(21) Appl. No.: 12/607,309

(22) Filed: Oct. 28, 2009

(65) Prior Publication Data

US 2011/0097007 A1    Apr. 28, 2011

(51) Int. Cl.
*G06K 9/00* (2006.01)

(52) U.S. Cl.
USPC .......................................... 382/128; 382/131

(58) Field of Classification Search
None
See application file for complete search history.

(56) References Cited

U.S. PATENT DOCUMENTS

| | | | | |
|---|---|---|---|---|
| 3,742,513 A * | 6/1973 | Ehrenspeck | | 343/817 |
| 4,905,148 A * | 2/1990 | Crawford | | 382/131 |
| 5,898,793 A * | 4/1999 | Karron et al. | | 382/131 |
| 5,963,211 A * | 10/1999 | Oikawa et al. | | 345/424 |
| 6,724,856 B2 | 4/2004 | De Man | | |
| 6,907,102 B1 * | 6/2005 | Sauer et al. | | 378/19 |
| 7,227,982 B2 | 6/2007 | De Man | | |
| 7,778,493 B2 * | 8/2010 | Ho et al. | | 382/299 |
| 2002/0142367 A1 * | 10/2002 | Ke et al. | | 435/40.5 |
| 2004/0081279 A1 * | 4/2004 | Brunnett | | 378/98.8 |
| 2005/0192764 A1 * | 9/2005 | Holland | | 702/28 |
| 2006/0067461 A1 * | 3/2006 | Yin et al. | | 378/5 |
| 2006/0204076 A1 * | 9/2006 | Avinash et al. | | 382/154 |
| 2007/0248265 A1 * | 10/2007 | Lundstrom et al. | | 382/168 |
| 2007/0297660 A1 | 12/2007 | Hsieh et al. | | |
| 2008/0075227 A1 * | 3/2008 | Christoph et al. | | 378/23 |
| 2009/0190814 A1 * | 7/2009 | Bouman et al. | | 382/131 |
| 2010/0172472 A1 * | 7/2010 | Ermes | | 378/62 |

OTHER PUBLICATIONS

Do et al., Accurate Model-Based High Resolution Cardiac Image Reconstruction in Dual Source CT, Jun. 2009, IEEE International Symposium on Biomedical Imaging, Boston, MA.

De Man, "Iterative reconstruction for reduction of metal artifacts in computed tomography," 2001, PhD Thesis, University of Leu.

(Continued)

*Primary Examiner* — Michelle Entezari
(74) *Attorney, Agent, or Firm* — Ziolkowski Patent Solutions Group, SC

(57) ABSTRACT

An improved iterative reconstruction method to reconstruct a first image includes generating an imaging beam, receiving said imaging beam on a detector array, generating projection data based on said imaging beams received by said detector array, providing said projection data to an image reconstructor, enlarging one of a plurality of voxels and a plurality of detectors of the provided projection data, reconstructing portions of the first image with the plurality of enlarged voxels or detectors, and iteratively reconstructing the portions of the first image to create a reconstructed image.

32 Claims, 18 Drawing Sheets

(56) References Cited

OTHER PUBLICATIONS

Synder, "Deblurring subject to nonnegativity constraints," Transactions on Medical Imaging, 1992, pp. 1143-1150, vol. 40, No. 5, IEEE.

Lewitt, "Multideminsional image representations using generalized Kaiser-Bessel window functions," Journal of Optical Society of America, 1990, pp. 1834-1846, vol. 7, Optical Society of America.

Browne et al, "Maximum-likelihood x-ray computed-tomography finite-beamwidth considerations," Journal of Applied Optics, 1995, pp. 5199-5209, vol. 32, No. 23, Optical Society of America.

Snyder, "Noise and edge artifacts in maximum-likelihood reconstructions for emission topography," Transactions on Medical Imaging, 1987, pp. 228-238, vol. MI-6, No. 3, IEEE.

Matej, "Practical considerations for 3-D image reconstruction using spherically symmetric volume elements," Transactions of Medical Imaging, 1996, pp. 68-78, vol. 15, IEEE.

\* cited by examiner

PSF for

PSF for ⟶ 1701

PSF in x and y directions
x-FWHM = 0.428mm, x-FWTM = 0.69mm
y-FWHM = 0.411mm, y-FWTM = 0.63mm

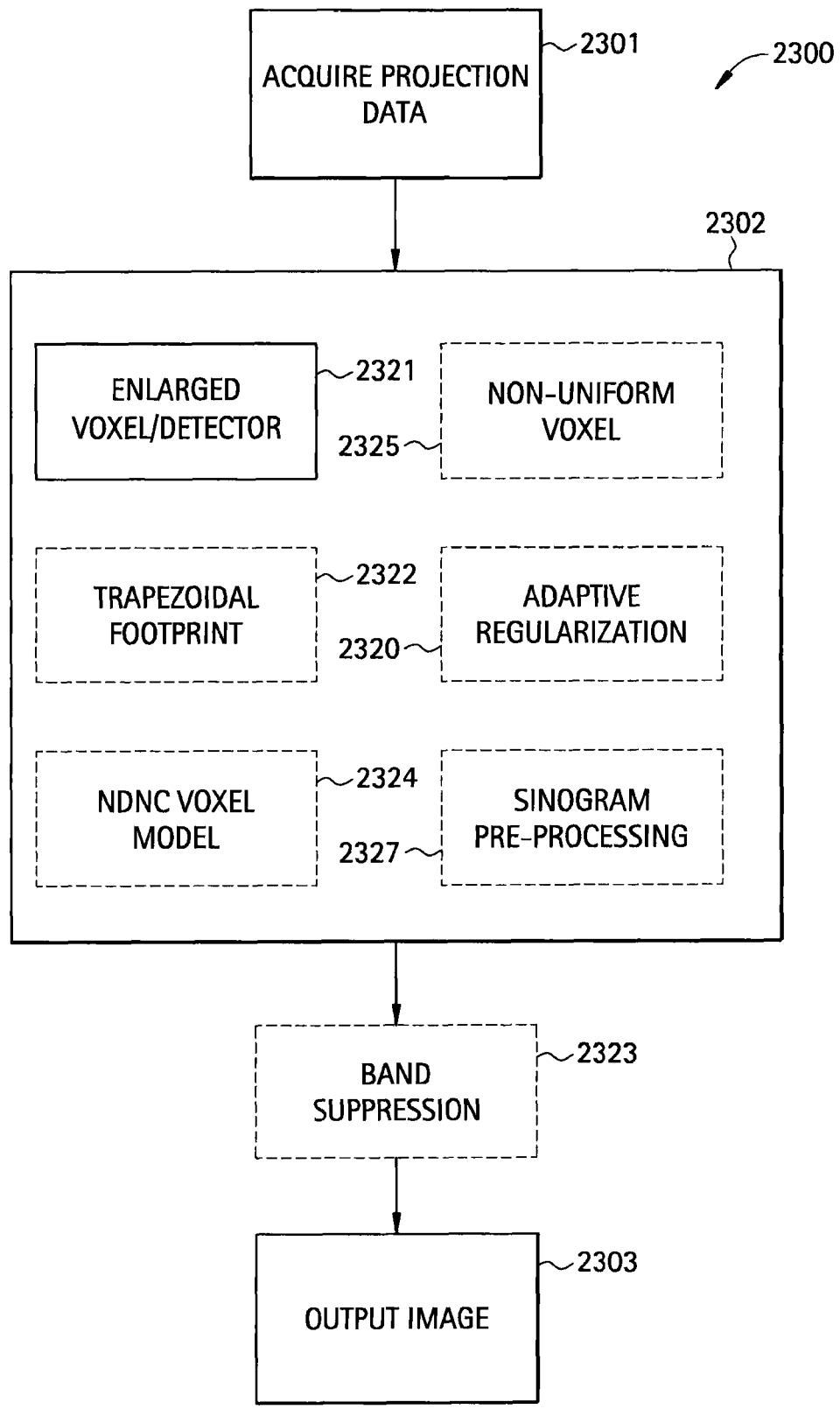

ITERATIVE RECONSTRUCTION

BACKGROUND OF THE INVENTION

The subject matter disclosed herein relates to medical imaging, and more particularly, to improved iterative reconstruction methodologies in medical imaging.

A computed tomography (CT) imaging system typically includes an imaging beam source (e.g., x-ray source or other suitable source) that projects fan- or cone-shaped imaging beams through an object being imaged, such as a patient, to an array of radiation detectors. The beam is collimated to lie within an X-Y plane, or to cover a set of such planes generally referred to as the "imaging planes." Intensity of radiation from the beam received at the detector array depends on attenuation of the imaging beam by the object. Attenuation measurements from each detector are acquired separately to produce a transmission profile.

The imaging beam source and the detector array are rotated within a gantry and around the object to be imaged so that a projection angle at which the imaging beam intersects the object constantly changes. A group of imaging beam attenuation measurements (such as integral projection data from the detector array at one gantry angle) is referred to as a "view". A "scan" of the object comprises a set of views made at varying projection angles, during one or more revolutions of the imaging beam source and detector array.

In an axial scan, the projection data is processed to construct an image that corresponds to one or more two-dimensional slices or other patterns taken through the object. To form these slices or patterns, iterative reconstruction of a full field of view may be performed to increase image quality. Iterative reconstruction refers to a method that forms an image by repeatedly adjusting an existing estimate according to the quality of a match between measured data and simulated measurements from a current estimate of the image. The quality of the image estimate may also be affected by consideration of the characteristics of the image alone, such as its smoothness and/or satisfaction of a pre-established model. Multiple iterations are performed to create a resulting reconstructed image that approximately matches the acquired projection data. A full set of reconstructed images is referred to as a 3-D reconstruction, because the set is formed into a three dimensional representation of the object with each image pixel or picture element corresponding to a single voxel or volume element in the 3-D reconstruction.

Traditionally, direct analytical algorithms, such as the Filtered Back-Projection (FBP) algorithm, have been used to reconstruct images from CT data. Iterative techniques, such as the Maximum A Posteriori Iterative Coordinate Descent (MAP-ICD) algorithm, have also been recently considered for reconstruction of volumetric CT data to provide means to improve general image quality over conventional techniques. It has been demonstrated that reduced noise, enhanced resolution, better low contrast performance, and reduced artifacts, can all be achieved with iterative reconstruction of clinical images.

However, Iterative reconstruction (IR) is not yet available on commercial scanners, which typically use the analytical FBP algorithm or its variants. To enable clinical use, current IR may need to better compete with the spatial resolution properties and artifact level of FBP.

BRIEF DESCRIPTION OF THE INVENTION

According to an example embodiment, an improved iterative reconstruction method to reconstruct a first image includes generating an imaging beam, receiving said imaging beam on a detector array, generating projection data based on said imaging beams received by said detector array, providing said projection data to an image reconstructor, enlarging one of a plurality of voxels and a plurality of detectors of the provided projection data, reconstructing portions of the first image with the plurality of enlarged voxels or detectors, and iteratively reconstructing the portions of the first image to create a reconstructed image.

According to another example embodiment, an imaging system includes a source generating an imaging beam, a detector array receiving said imaging beam and generating projection data, a translatable table configured for disposal of an object thereon and operable to translate in relation to said source and said detector array, said source and said detector array rotating about said translating table to helically scan said object, and an image reconstructor electrically coupled to said detector array, said image reconstructor having a processor responsive to computer executable instructions that, when executed on the processor, direct the processor to perform an improved iterative reconstruction method to reconstruct a first image in response to said projection data. The method includes enlarging one of a plurality of voxels and a plurality of detectors of the provided projection data, reconstructing portions of the first image with the plurality of enlarged voxels or detectors, and iteratively reconstructing the portions of the first image to create a reconstructed image.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

FIG. 23 is a flowchart of a method of improved iterative reconstruction, according to an example embodiment.

Figure 1:
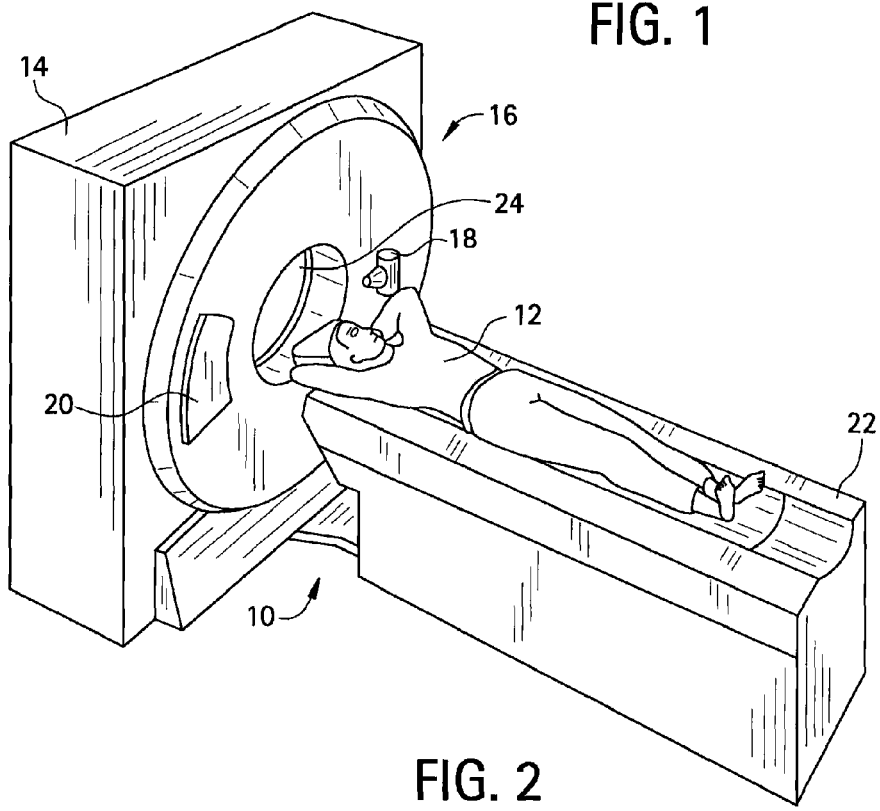
FIG. 1 is a pictorial view of an imaging system utilizing a method of reconstructing an image in accordance with an embodiment of the present invention.

The detailed description explains embodiments of the invention, together with advantages and features, by way of example with reference to the drawings.

DETAILED DESCRIPTION OF THE INVENTION

Detailed illustrative embodiments are disclosed herein. However, specific functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments.

It will be understood that, although the terms first, second, etc. may be used herein to describe various steps or calculations, these steps or calculations should not be limited by these terms. These terms are only used to distinguish one step or calculation from another. For example, a first calculation could be termed a second calculation, and, similarly, a second step could be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting of example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

It should also be noted that where the definition of terms departs from the commonly used meaning of the term, applicant intends to utilize the definitions provided below, unless specifically indicated.

As used herein, the term "voxel" refers to a unit element representing a volumetric pixel achieved through imaging information acquired through use of an imaging system, but can also refer to other basis functions, such as blobs.

As used herein, the term "image space" refers to a set of vectors arranged in an array for use with a method of the present invention. The array may be of any number of dimensions, such as two-dimensional, three-dimensional, four-dimensional, for example. An example of an image space that may be used in a method described herein is a set of all possible images representable on a lattice of a given dimension. A single element (vector) of the set of the image space may be viewed on a visual display apparatus to allow a user to gain information of the interior of a scanned object.

As used herein, the term "forward model" refers to a description of the transformation from the image space of a scanned object to the projection space for a scanned object, as modeled after the operation of the CT imaging system. The operation of the forward model on an image vector is referred to as "forward projection."

As used herein, the term "computed tomography model" refers to a mathematical description of the relation between a vector in the image space and a vector in the projection space. A computed tomography model includes a forward model and a cost function chosen to evaluate the closeness of a match between a projection vector and a forward projection of an image vector by a forward model.

As used herein, the term "projection space" refers to a set of vectors of integral imaging beam attenuation values. The vectors that make up a projection space may comprise data from an imaging system. Also, the vectors that make up a projection space may be forward projections of vectors from an image space. It is understood that the projections may also be represented as signal intensities, in which case the forward model typically also includes an exponentiation commonly referred to as Beer's law.

As used herein, the term "visual display device" refers to any type of device such as a CRT monitor, LCD screen, projected image, etc. used to visually inspect multidimensional vectors.

As used herein, the term "multi-slice computed tomography imaging system" refers to an imaging system in which a detector array contains multiple rows of detectors, each row occupying a different position along the axis of the system about which the gantry rotates.

As used herein, the term "filtered back projection" refers to a technique of reconstructing images from projection data by processing data in the projection space, then forming the value of each element in the image space as a linear combination of values from processed data, those values taken from projection space points to which the given image element contributes in forward projection.

As used herein, the term "high quality reconstruction image" refers to an image space vector whose accuracy as a representation of the object under study is comparable to those produced by currently available commercial CT imaging systems and known in the art.

While example embodiments of the present invention are described with respect to apparatus and methods of reconstructing an image using iterative techniques for an imaging system (such as a multi-slice CT imaging system), the following apparatuses and methodologies are capable of being adapted for various purposes including, but not limited to the following applications: magnetic resonance imaging (MRI) systems, CT systems, radiotherapy systems, x-ray imaging systems, ultrasound systems, nuclear imaging systems, positron emission tomography (PET) systems, magnetic resonance spectroscopy systems, and other applications known in the art, such as but not limited to applications outside medical imaging such as nondestructive testing, geological and astronomical imaging, and in general a large class of inverse problems.

Example embodiments of the present invention may provide benefits including improved image quality of iteratively reconstructed images, especially in terms of spatial resolution, over/undershoots and aliasing artifacts. As is described more fully below, example embodiments provide methodologies which may include a combination of one or more of increased voxel/detector size, trapezoidal response kernel (anti-symmetric functions for general cases), band-suppression post-processing technique, neighborhood-dependent non-constant voxel model (NDNC), adaptive regularization for iterative reconstruction, general sinogram preprocessing, and iterative reconstruction for focal spot wobbling geometry.

Referring now to FIG. 1, a pictorial view of an imaging system 10 utilizing a method of reconstructing an image of medical patient 12 in accordance with an embodiment of the present invention is shown. The imaging system 10 includes a gantry 14 that has a rotating inner portion 16 containing an imaging beam source 18 and a detector array 20. Imaging beam source 18 projects an imaging beam toward detector array 20. Source 18 and detector array 20 rotate about an operably translatable table 22. Table 22 is translated along the z-axis between source 18 and detector 20 to perform a helical scan. The beam, after passing through medical patient 12, within a patient bore 24, is detected at detector array 20 to generate projection data that is used to create a CT image.

Figure 2:
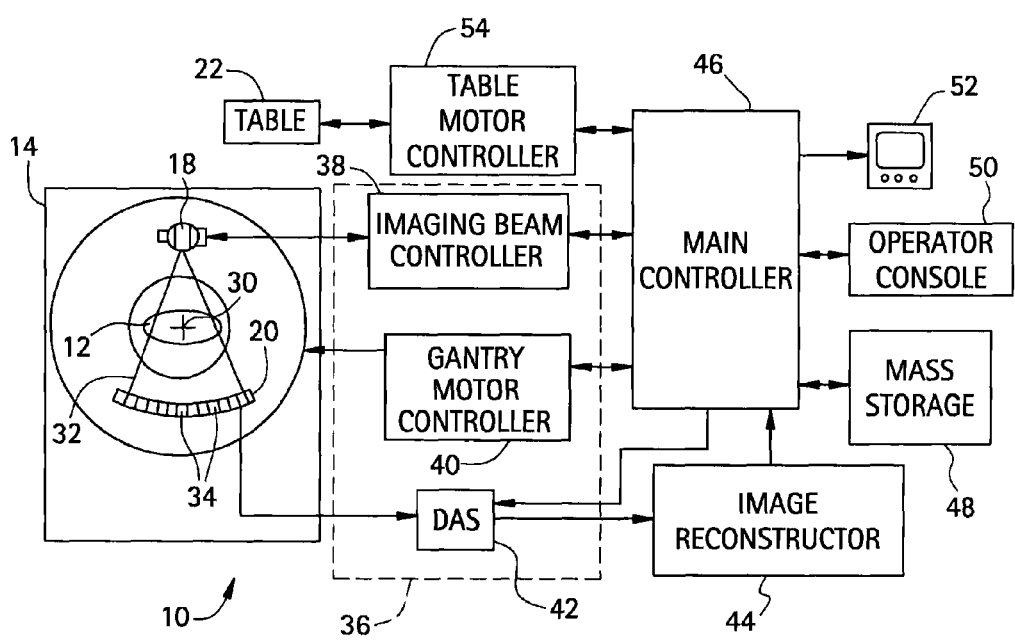
FIG. 2 is a block diagrammatic view of the imaging system in accordance with an embodiment of the present invention

Referring now to FIG. 2, a diagrammatic view of the imaging system 10 in accordance with an exemplary embodiment. Source 18 and detector array 20 rotate about a center axis 30. Beam 32 is received by multiple detector elements 34 in multiple detector rows. Each detector element 34 generates an electrical signal corresponding to the intensity of an impinging imaging beam. As beam 32 passes through patient 12, beam 32 is attenuated. Rotation of the center portion of the gantry and the operation of source 18 are governed by a control mechanism 36. Control mechanism 36 includes an imaging beam controller 38 that provides power and timing signals to imaging beam source 18 and a gantry motor controller 40 that controls the rotational speed and position of the center portion of the gantry. A data acquisition system (DAS) 42 samples analog data from detector elements 34 and converts the analog data to digital signals for subsequent processing. An image reconstructor 44 receives sampled and digitized imaging beam data from DAS 42 and performs image reconstruction. A main controller 46 stores the image in a mass storage device 48.

Main controller 46 also receives commands and scanning parameters from an operator via an operator console 50. A display 52 allows the operator to observe the reconstructed image and other data from main controller 46. The operator supplied commands and parameters are used by main controller 46 in operation of DAS 42, imaging beam controller 38, and gantry motor controller 40. In addition, main controller 46 operates a table motor controller 54, which translates table 22 to position patient 12 in gantry 14.

Imaging beam controller 38, gantry motor controller 40, image reconstructor 44, main controller 46, and table motor controller 54 are preferably based on micro processors device capable of accepting data and instructions, executing the instructions to process the data, and presenting the results, such as a computer having a central processing unit, memory (nonvolatile, random-access, and/or read-only), and associated input and output buses. Imaging beam controller 38, gantry motor controller 40, image reconstructor 44, main controller 46, and table motor controller 54 may be a portion of a central control unit or may each be a discrete, stand-alone components as shown. Therefore, the imaging beam controller 38, gantry motor controller 40, image reconstructor 44, and main controller 46 can be a microprocessor, microcomputer, a minicomputer, an optical computer, a board computer, a complex instruction set computer, an ASIC (application specific integrated circuit), a reduced instruction set computer, an analog computer, a digital computer, a molecular computer, a quantum computer, a cellular computer, a superconducting computer, a supercomputer, a solid-state computer, a single-board computer, a buffered computer, a computer network, a desktop computer, a laptop computer, a scientific computer or a hybrid of any of the foregoing.

Figure 21:
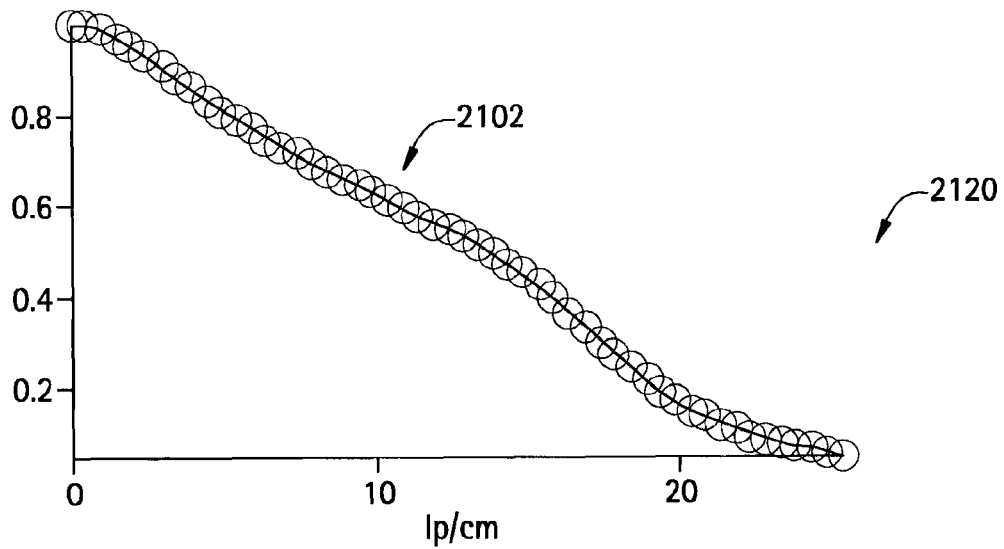
FIG. 21 illustrates a filtered modulation transfer function of the response of an imaging system employing enlarged voxel model iterative reconstruction, according to an example embodiment

Imaging beam controller 38, gantry motor controller 40, image reconstructor 44, and main controller 46 also include operation control methods embodied in application code, such as that shown in FIG. 21 for example. These methods are embodied in computer instructions written to be executed by a processor, typically in the form of software. The software can be encoded in any language, including, but not limited to, assembly language, VHDL (Verilog Hardware Description Language), VHSIC HDL (Very High Speed IC Hardware Description Language), Fortran (formula translation), Pascal, PL/I. C, C++, Visual C++, C#, Java, ALGOL (algorithmic language), BASIC (beginners all-purpose symbolic instruction code), visual BASIC and any combination or derivative of at least one of the foregoing. Additionally, an operator can use an existing software application such as a spreadsheet or database and correlate various cells with the variables enumerated in the algorithms. Furthermore, the software can be independent of other software or dependent upon other software, such as in the form of integrated software.

Figure 3:
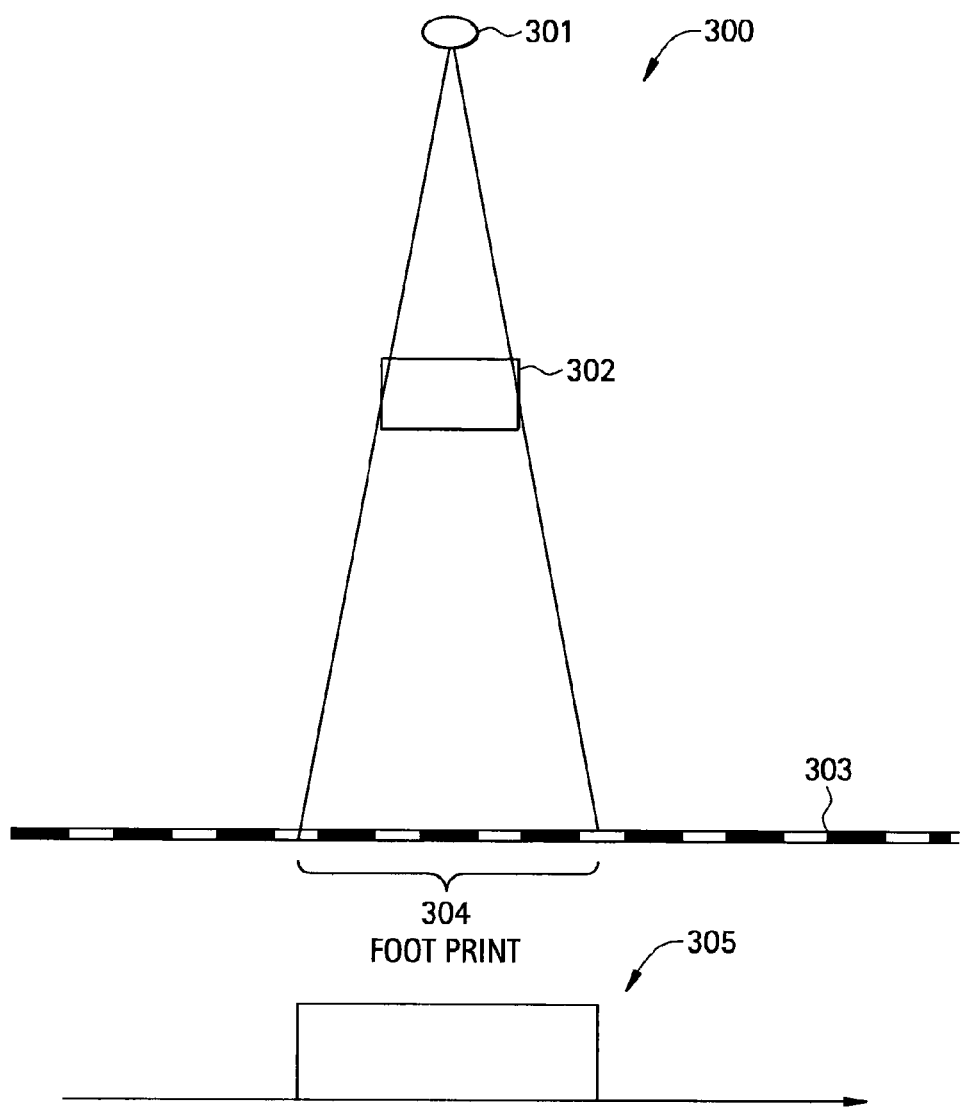
FIG. 3 is a diagram of a simplified ideal imaging system with an infinitely small imaging beam focal spot, according to an example embodiment.

FIG. 3 is a diagram of a simplified imaging system, according to an example embodiment. As illustrated imaging system 300 includes a point source 301 and a detector array 303. The point source 301 may be a point source of radiation or an imaging beam configured to penetrate a body forming voxel 302 for imaging. Radiation emitted from the point source 301 passes through the body becoming attenuated, and is incident upon the detector array 303. The incident radiation may form footprint 304, representing the projection of voxel 302. It is noted that a true point source is an ideal case, one for which a final reconstructed image may be compared upon implementation of iterative methodologies as described herein. In a real case, there may be influences which cause disturbances on a footprint.

Figure 4:
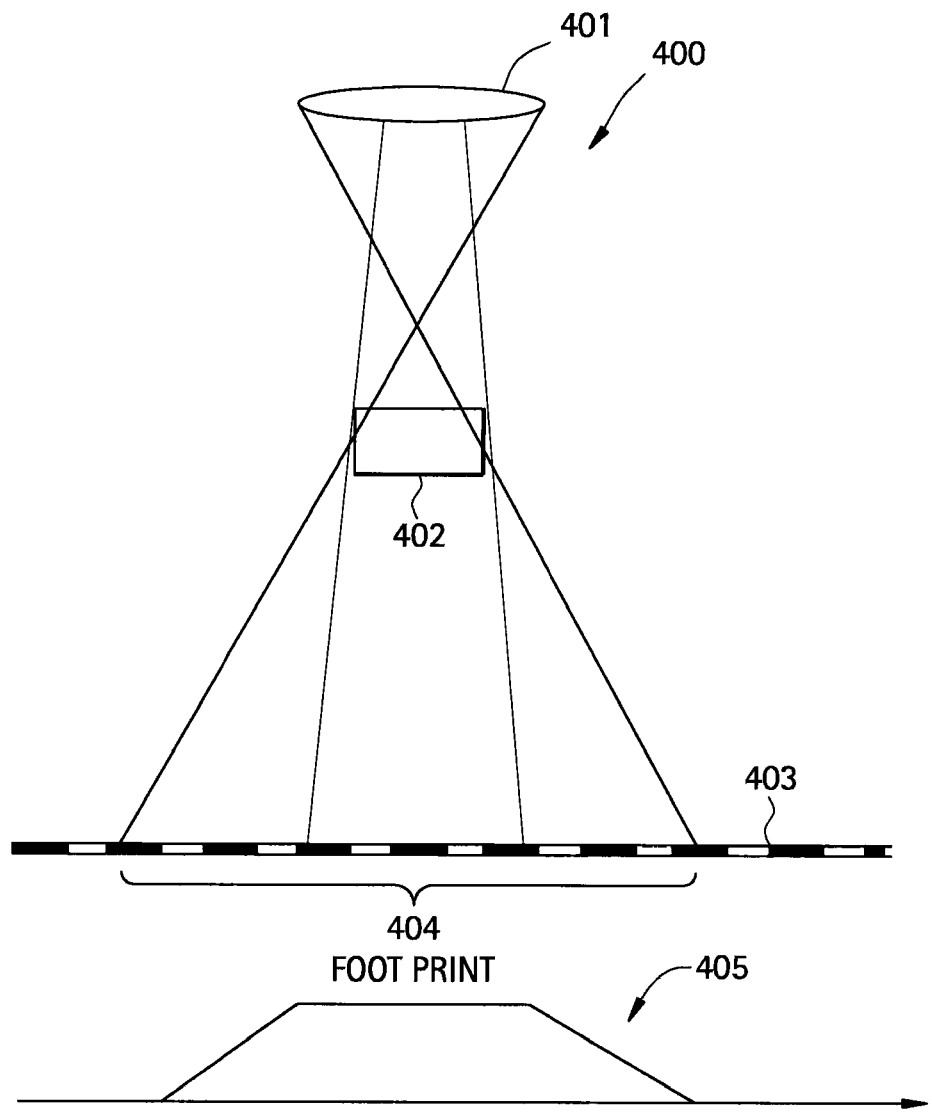
FIG. 4 is a diagram of a simplified real imaging system with a finite size imaging beam focal spot, according to an example embodiment.

FIG. 4 is a diagram of a simplified imaging system, according to an example embodiment. As illustrated imaging system 400 includes a finite source 401 and a detector array 403. The finite source 401 may be a finite source of radiation or an imaging beam configured to penetrate a body forming voxel 402 for imaging. Radiation emitted from the finite source 401 passes through the body becoming attenuated, and is incident upon the detector array 403. However, as the source 401 is a finite source, a plurality of incoherent radiation paths may exist from the finite source 401 and the detector array 403. Thus, the incident radiation may form a footprint 404 which includes cross-talk, convolution, and/or blurring due to the size of the finite source 401. This cross-talk, convolution, and/or blurring may reduce the resolution of voxel 402. Further, conventional models of finite beam width typically include summing rays corresponding to multiple sample points on the focal spot, multiple sample points on the detector, and multiple small rotation increments within one view.

However, according to example embodiments of the present invention, techniques for increasing or boosting resolution are provided which may emulate the convolution (blurring) effects of finite focal spot in real imaging system with enlarged voxel/detector models. It is noted that although the terms cross-talk and blurring are used as examples of interference, example embodiments are applicable to any form of detector interference. For example, "rotation" blur, finite x-ray/imaging beam focal spot size, gaps between detector cells, detector misalignments, and other interference may be reduced with example embodiments. Since any deviation of the model from reality incurs a penalty in terms of spatial resolution for the reconstructed images, improving model accuracy by means of enlarged voxels/detectors improves spatial resolution recovery.

Figure 5:
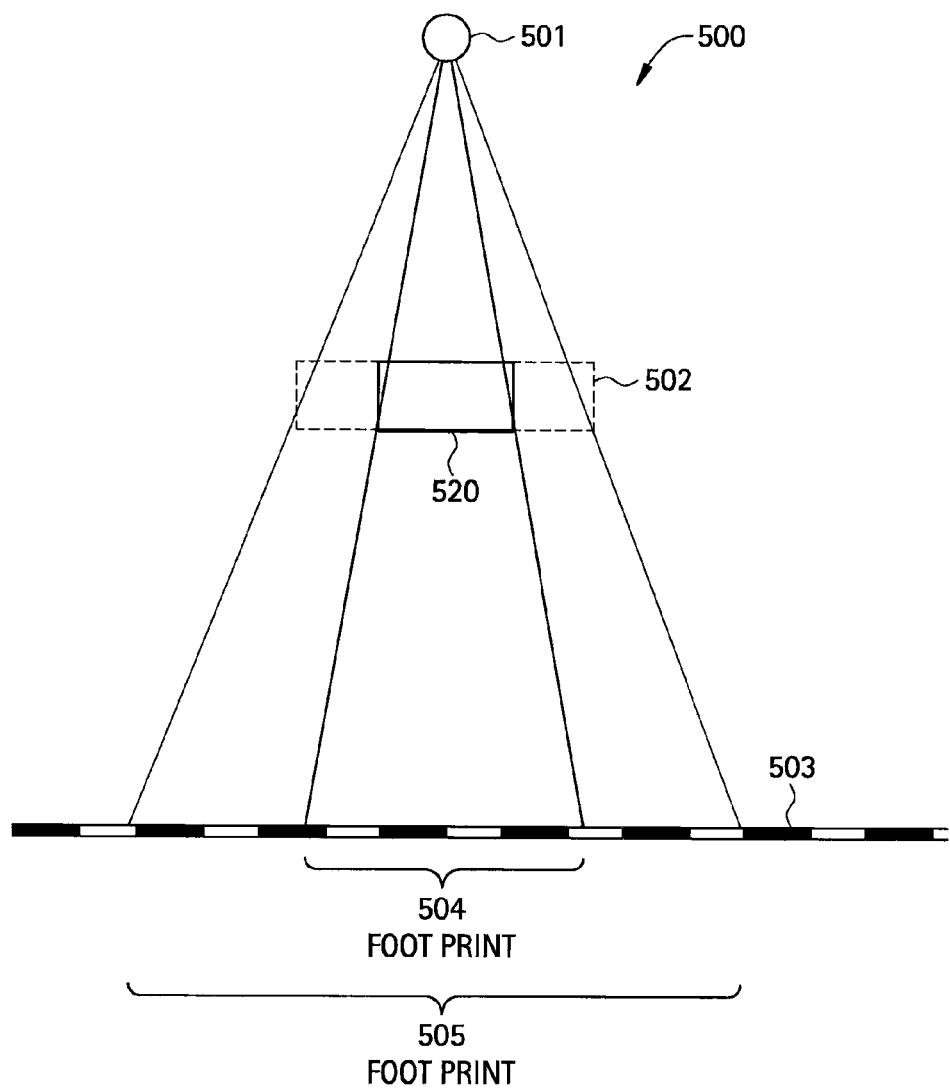
FIG. 5 is a diagram of a simplified imaging system with an enlarged voxel model, according to an example embodiment.

FIG. 5 is a diagram of a simplified imaging system, according to an example embodiment. The illustrated imaging system 500 includes a source 501 and a detector array 503. The source 501 may be a source of radiation or an imaging beam configured to penetrate a body creating voxel 520 for imaging. Radiation emitted from the source 501 passes through the body becoming attenuated, and is incident upon the detector array 503. As further illustrated, portion 520 of voxel 502 represents a typical imaging body voxel as described in FIGS. 3-4. However, the size of voxel 502 is greater than conventional voxels 302 and 402. Thus, the incident radiation may form footprint 505 which models blurring or convolution from finite size focal spot. It is noted that the voxel size is assumed to be larger than the voxel spacing due to the conventional size of voxels (i.e., there is some overlap between neighboring voxels). The inclusion of this model may mitigate the blurring effect.

Alternatively or in combination with increased voxel sizes, detector sizes may also be increased to emulate the blurring effect in the forward projection. It is noted that as used herein, increasing a detector size means the detector aperture modeled in a reconstruction algorithm is larger than its true physical aperture.

Figure 6:
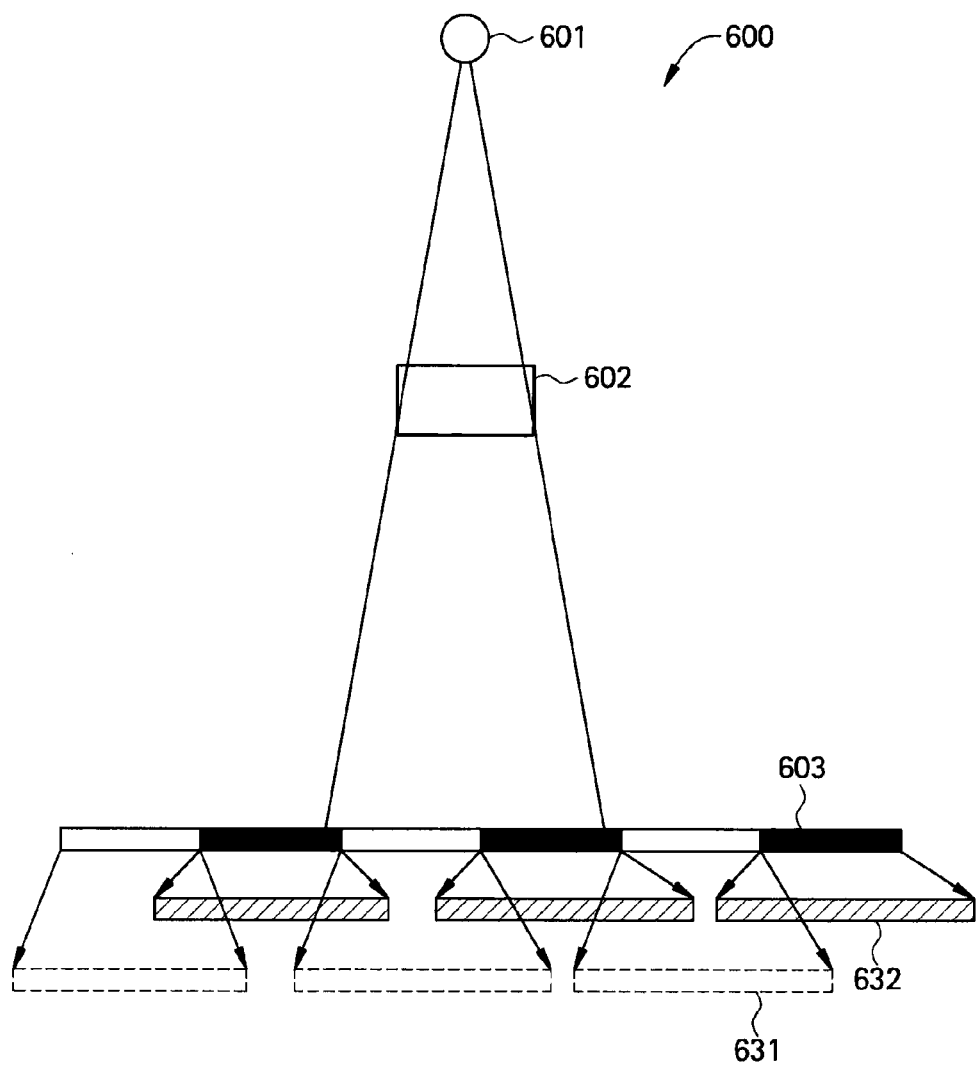
FIG. 6 is a diagram of a simplified imaging system with an enlarged detector model, according to an example embodiment.

FIG. 6 is a diagram of a simplified imaging system, according to an example embodiment. As illustrated imaging system 600 includes a source 601 and a detector array 603. The source 601 may be a source of radiation or an imaging beam configured to penetrate a body creating voxel 602 for imaging. Radiation emitted from the source 601 passes through the body becoming attenuated, and is incident upon the detector array 603. As further illustrated, detector array 603 includes enlarged detectors (631-632) which are relatively larger than conventional detectors as described in FIGS. 3-5. Thus, as the size of the detectors within detector array 603 are larger. Thus, the incident radiation may form a footprint which includes the effects of finite source blurring, but also achieves a higher resolution thereby. Furthermore, when modeling detector blur (e.g., due to cross-talk, finite focal spot size, etc.) the detector cell size is assumed/modeled to be larger than the detector cell spacing (i.e., there is some overlap between neighboring detector cells).

Hereinafter configurations and responses for rectangular and trapezoidal voxel and detector models are described with reference to FIGS. 7-9.

Figure 7:
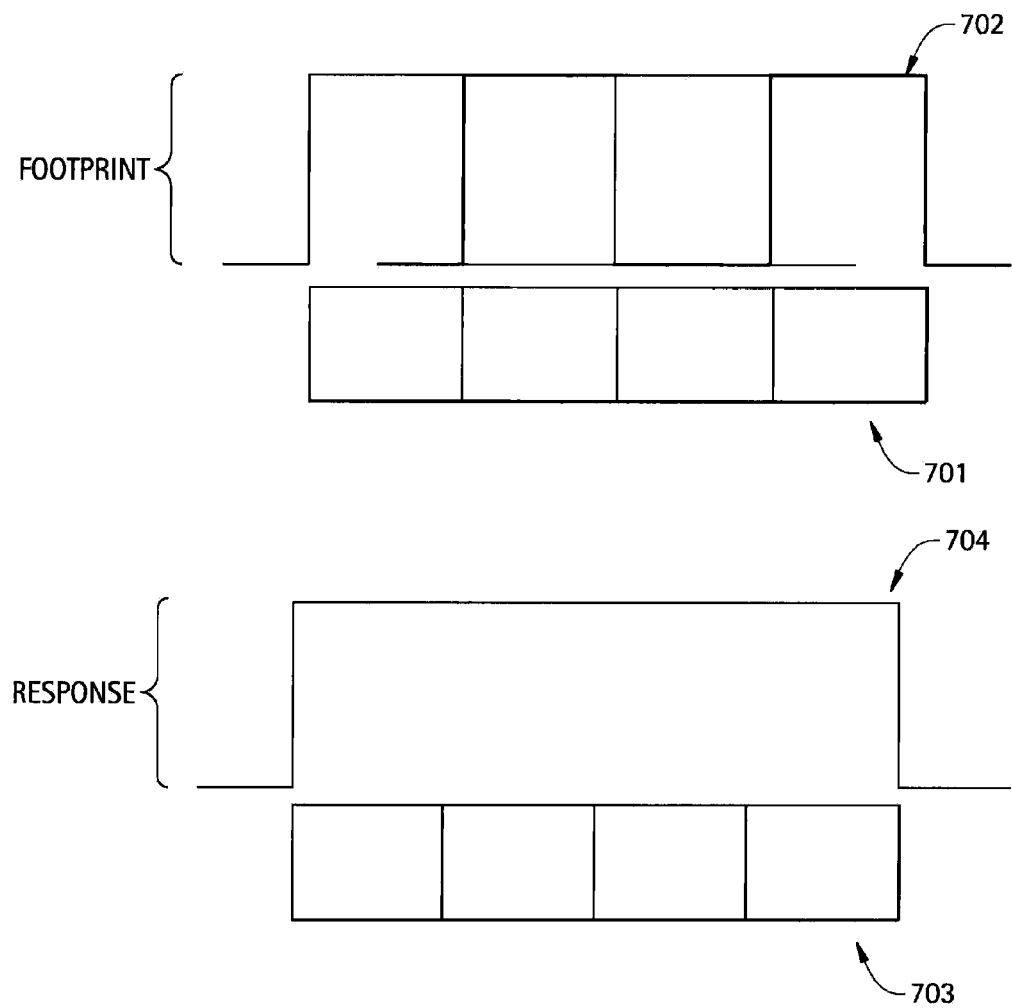
FIG. 7 illustrates a configuration and response of a voxel and detector of an imaging system.

FIG. 7 illustrates a configuration and response of a voxel and detector of an imaging system based upon conventional voxel and detector sizes. As illustrated, the voxel/detector configuration 701 has a footprint 702 that results in a relatively smooth response pattern 703-704. More clearly, as voxel and detector sizes are of conventional sizes, and are rectangular when modeled, a smooth rectangular response 704 is achieved. However, example embodiments provide increased size for voxels and/or detectors, which alters a response based on a configured footprint for the voxels and detectors.

Figure 8:
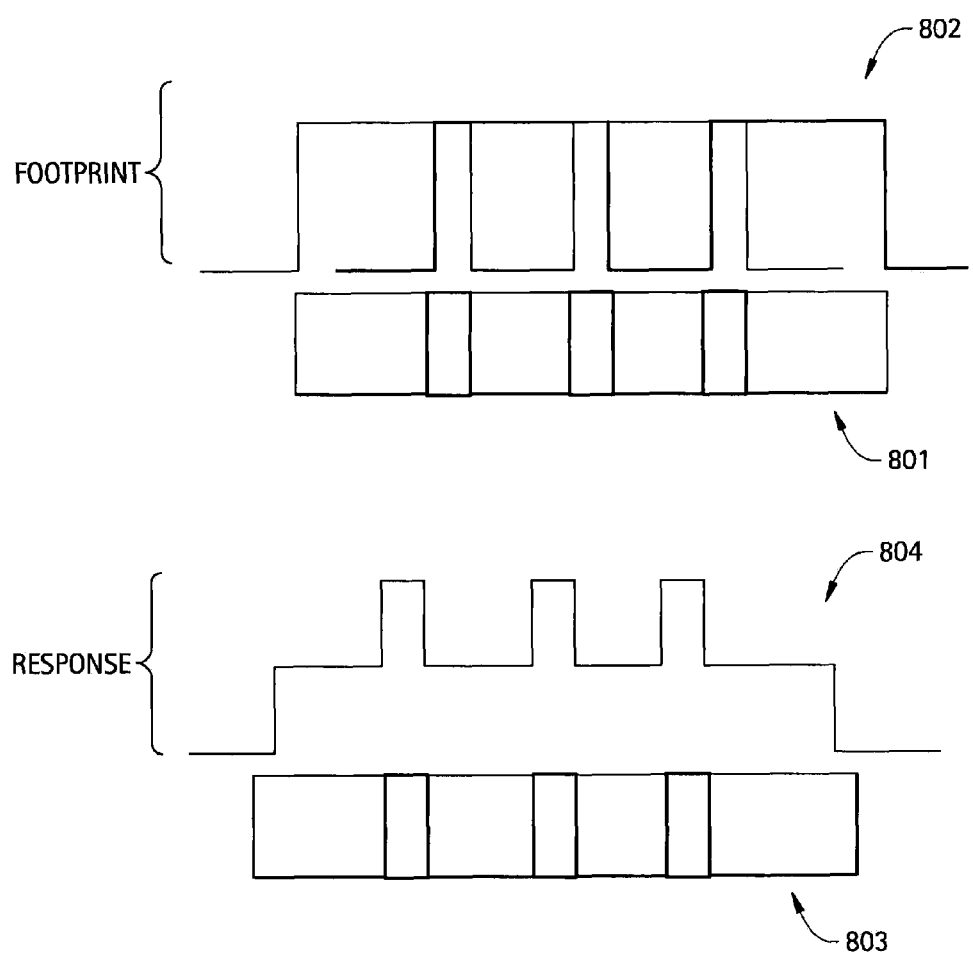
FIG. 8 illustrates a configuration and response of an enlarged rectangular voxel and detector of an imaging system, according to an example embodiment.

FIG. 8 illustrates a configuration and response of a voxel and detector of an imaging system, according to an example embodiment. As illustrated, the voxel/detector configuration 801 results in an overlapping rectangular footprint 802 which may introduce peaks in the response 804. For example, for a distance-driven projector and/or back-projector technique, two voxel boundaries may be mapped onto an axis or onto the detector to generate a rectangular footprint of said voxels. Rectangular voxel profiles are the conventional model for 3D voxels. From this rectangular footprint, the overlap kernel computes a weight for the corresponding voxel-detector pairs. For example, as the voxels/detectors are of increased size compared to conventional arrangements, but the physical spacing is the same, there is overlap which increases the response at regular intervals representing the overlap of each voxel/detector. Thus, in order to reduce the peaks in effort to smooth the response, a trapezoidal footprint configuration may be used for the detectors/voxels.

Figure 9:
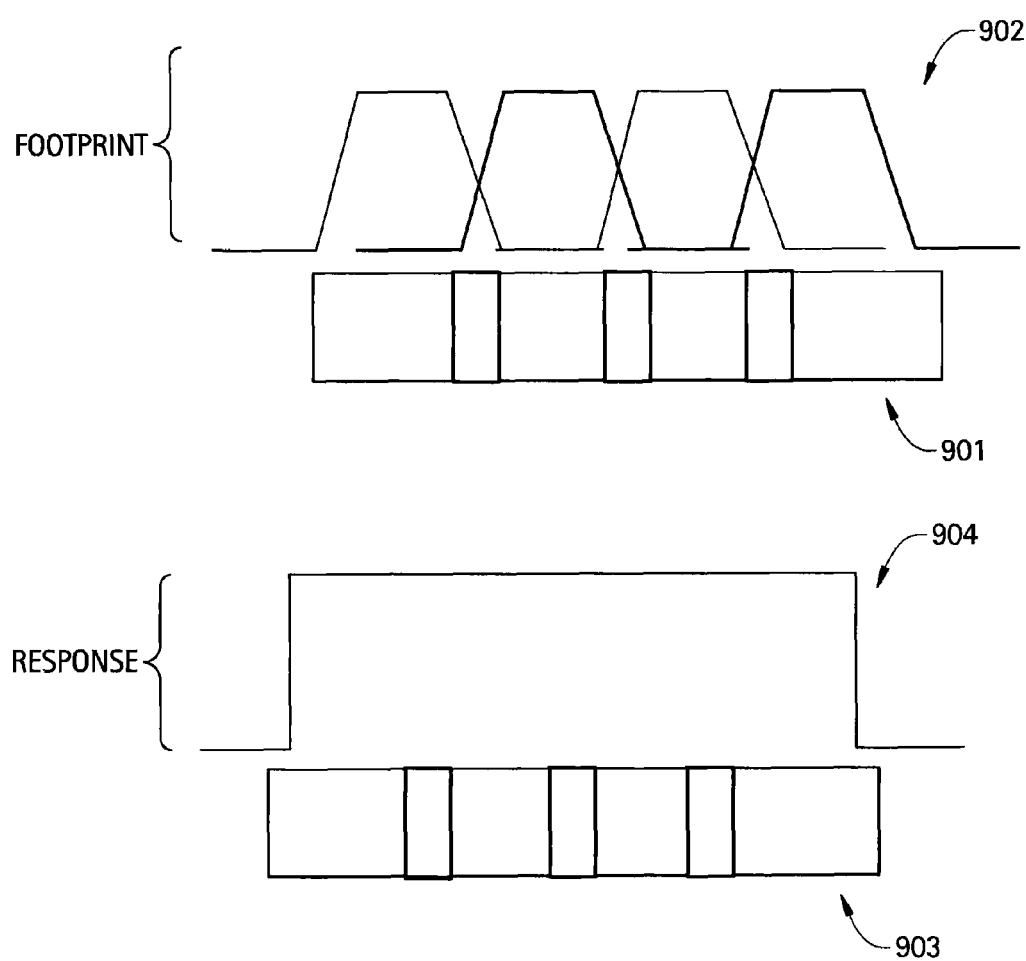
FIG. 9 illustrates a configuration and response of an enlarged trapezoidal voxel and detector of an imaging system, according to an example embodiment.

FIG. 9 illustrates a configuration and response of a voxel and detector of an imaging system, according to an example embodiment. As illustrated, the voxel/detector configuration 901 results in an overlapping trapezoidal footprint 902 which may reduce peaks in the response 904. For example, for a distance-driven projector and/or back-projector technique, two voxel boundaries may be mapped onto an axis or onto the detector to generate a trapezoidal footprint of said voxels. From this trapezoidal footprint, the overlap kernel computes a weight for the corresponding voxel-detector pairs. For example, as the voxels/detectors are of increased size compared to conventional arrangements, but the physical spacing is the same, there is overlap. However, the overlap is on the voxel/detector boundaries which are angular, thus, decreasing or eliminating the regular peaks shown in FIG. 8.

As described above, in contrast to FIG. 8, a trapezoidal footprint is used for the voxels as this more accurately represents the re-projection of a rectangular voxel onto the detector. Whereas such a model does incur some additional arithmetic cost, the overall computation can remain low, if a conventional kernel is used in an inner loop of an iterative reconstruction algorithm (typically the z-direction). This improved voxel profile can be applied in x, y or z or a combination thereof. Alternatively, the response of the detector cells may also be modeled by a trapezoidal profile in a similar way.

The combination of using a trapezoidal voxel footprint for voxels/detectors and a distance driven (or other) projection and back-projection technique may provide increased resolution. For example, the back-projection technique may be a distance-driven technique as described in U.S. Pat. No. 7,227,982 and U.S. Pat. No. 6,724,856, both of which are hereby incorporated by reference in their entirety. The distance-driven technique has two important aspects. A first aspect includes the mapping of the voxel and detector boundaries onto a common axis. A second aspect is the use of the overlap kernel for computation of the projection and backprojection coefficients. Thus, methodologies included herein may include an adaptation of the overlap kernel, which may still be used in combination with mapping boundaries onto a common axis. However, this technique is not limited to a distance-driven approach as described below, and instead may be applied to other forward & backward operations, such as pixel driven, ray driven and other techniques.

Figure 10:
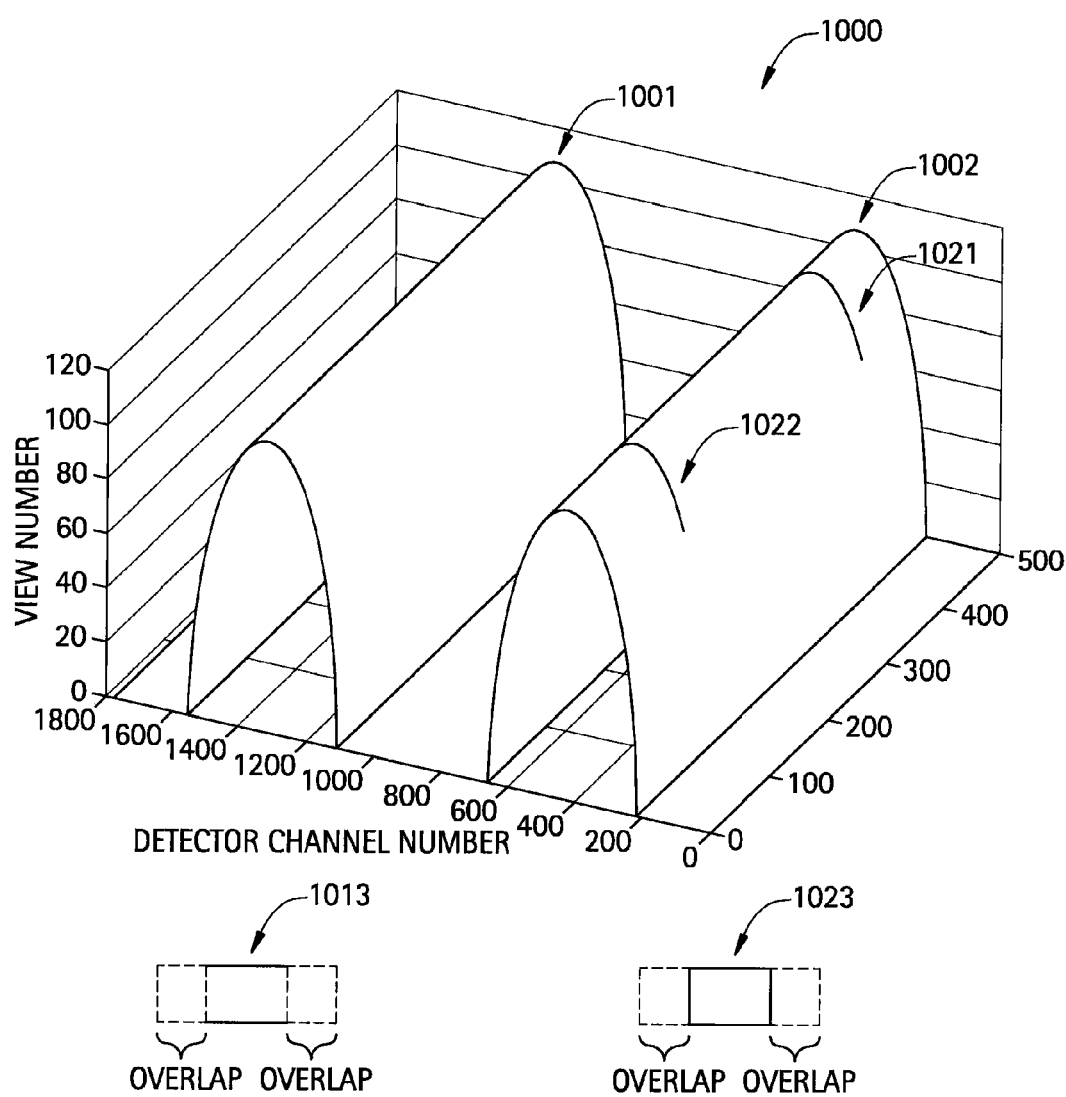
FIG. 10 is a graph of a forward projection of differing voxel and detector footprints, according to an example embodiment.

FIG. 10 is a graph of a forward projection of differing voxel and detector footprints, according to an example embodiment. As illustrated in graph 1000, the forward projection of rectangular configurations of voxels/detectors results in regular peaks depicted as disturbances 1021 and 1022 in the rectangular forward model curve 1002. For example, the rectangular voxel/detector model is represented by the model 1023 which includes references to overlaps associated with the larger rectangular voxels/detectors.

In contrast, the forward projection of trapezoidal configurations of voxels/detectors mitigates any peaks found in rectangular models as shown in the disturbance-free trapezoidal forward model curve 1001. For example, the trapezoidal voxel/detector model is represented by the model 1013 which includes references to overlaps associated with the larger trapezoidal voxels/detectors.

Figure 11:
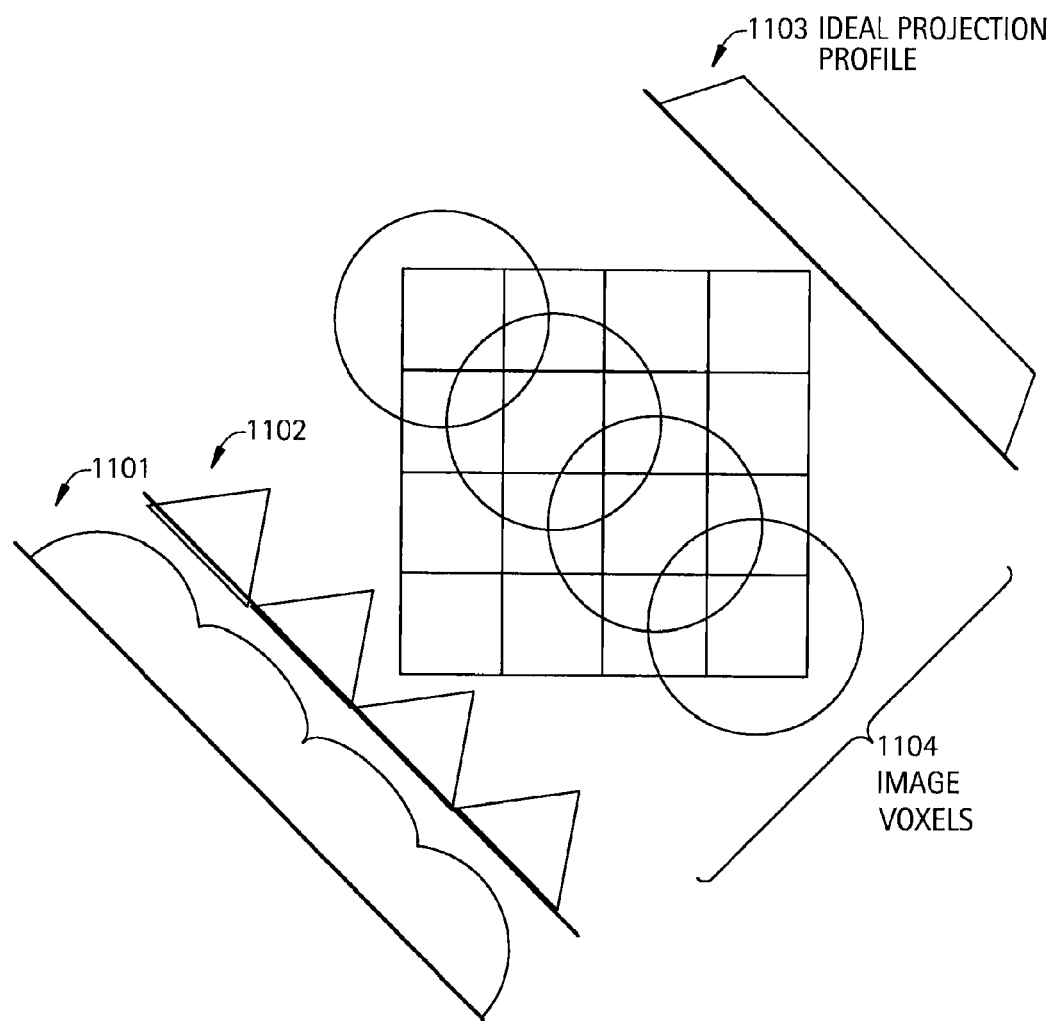
FIG. 11. is a diagram representing aliasing of a measured projection in an imaging system.

FIG. 11 is a diagram representing aliasing of a measured projection in an imaging system. As illustrated, the forward projection of an exemplary enlarged voxel/detector model 1101 includes smoother oblique edges when compared to the conventional uniform voxel/detector model 1102, thereby resulting in an ideal projection 1103 (see image voxels 1104) which is also smooth.

Figure 12:
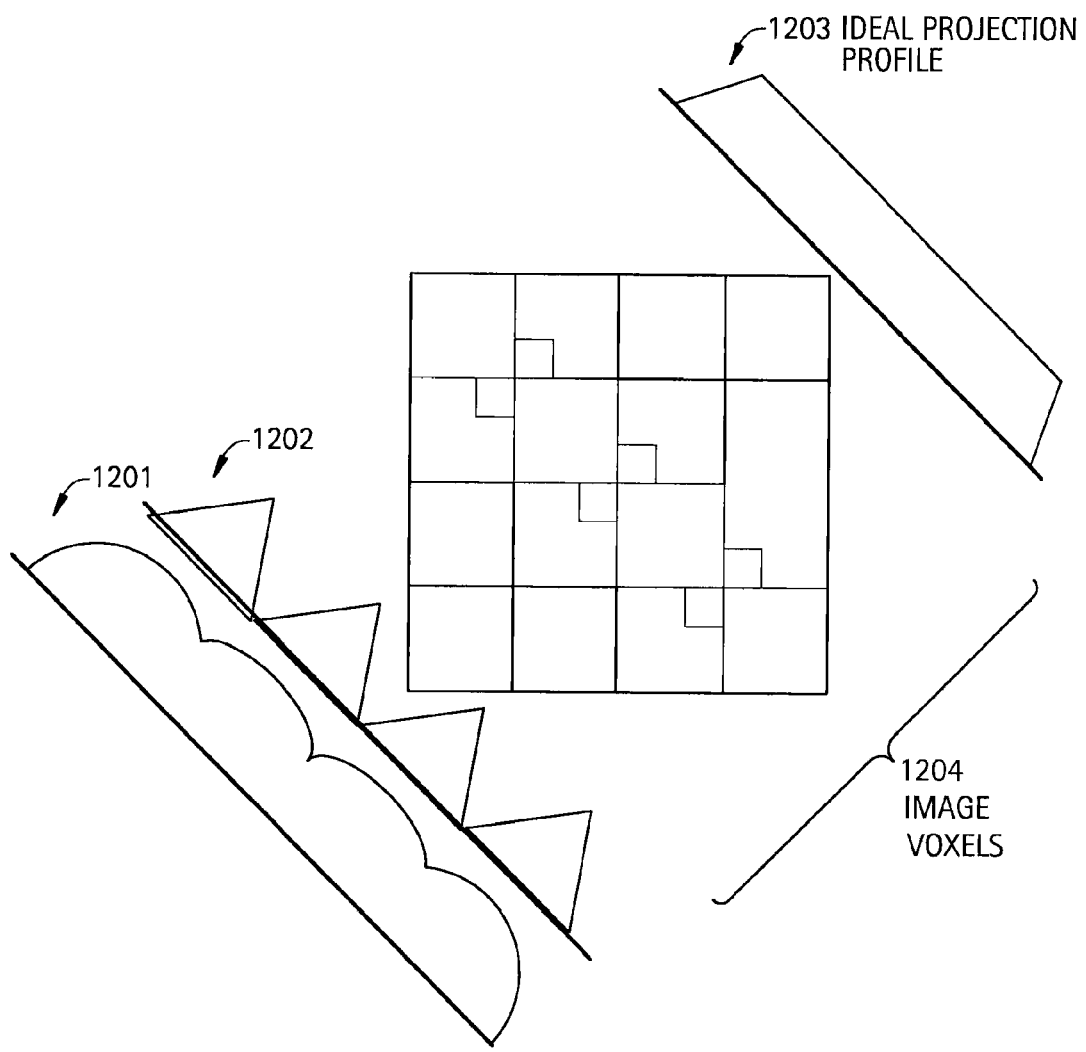
FIG. 12 is a diagram representing aliasing of a measured projection in an imaging system.

FIG. 12 is a diagram representing aliasing of a measured projection in an imaging system. As illustrated, the forward projection of non-uniform voxel model 1201 includes smoother oblique edges when compared to the conventional uniform voxel/detector model 1202, thereby resulting in an ideal projection 1203 (see image voxels 1204) which is also smooth.

Figure 13:
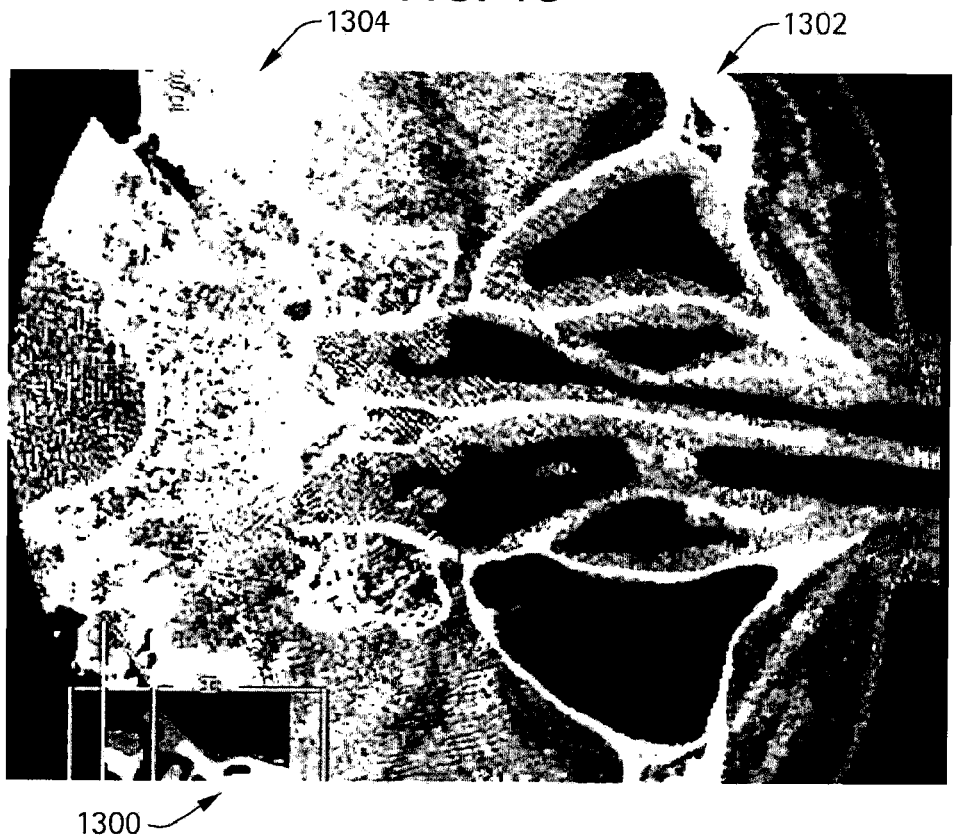
FIG. 13 illustrates a reconstructed image utilizing methods of improved iterative reconstruction, according to an example embodiment.
Figure 14:
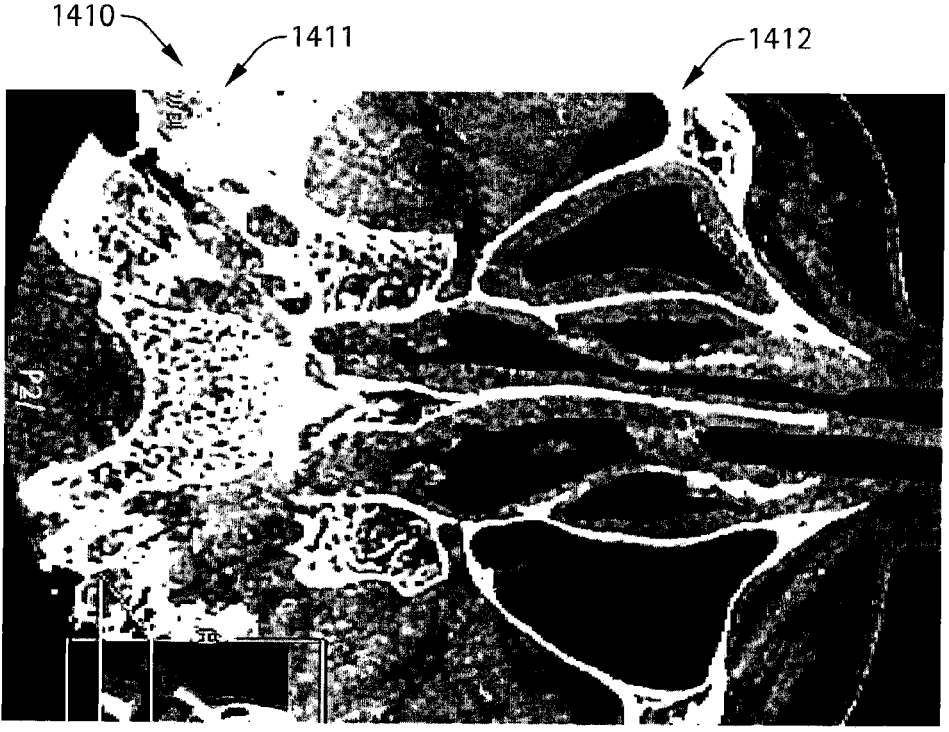
FIG. 14 illustrates a reconstructed image utilizing methods of improved iterative reconstruction, according to an example embodiment.

FIGS. 13 and 14 illustrate reconstructed images utilizing methods of improved iterative reconstruction, according to an example embodiment. As shown, image 1300, which was reconstructed using a conventional iterative reconstruction technique, includes lower resolution as outlined in areas 1304 and 1302 of the image 1300. However, the image 1410 which was reconstructed using an exemplary iterative reconstruction technique with enlarged voxels/detectors includes better resolution as outlined in areas 1411 and 1412 of the image 1410. Thus, it is readily apparent that the benefits of iterative reconstruction techniques as explained herein result in better image clarity and resolution compared to conventional iterative reconstruction techniques. Additionally, the aliasing artifacts are also reduced, as shown through the differences between FIGS. 13 and 14. More clearly, image 1300 includes a plurality of cross pattern line/streaks, which are suppressed in image 1410.

However, example embodiments of the present invention are not limited to enlarged and/or trapezoidal models for voxels/detectors. Hereinafter, additional techniques which may be combined with the discussed embodiments and provide further benefits over conventional techniques. For example, FIGS. 15-18 provide point spread function illustrations both before and after implementation of a band suppression filter configured to further increase image quality of iteratively reconstructed images.

Figure 15:
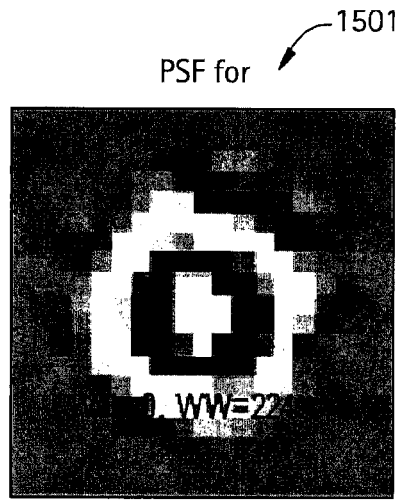
FIG. 15 illustrates a point spread function of the response of an imaging system employing enlarged voxel model iterative reconstruction, according to an example embodiment.
Figure 16:
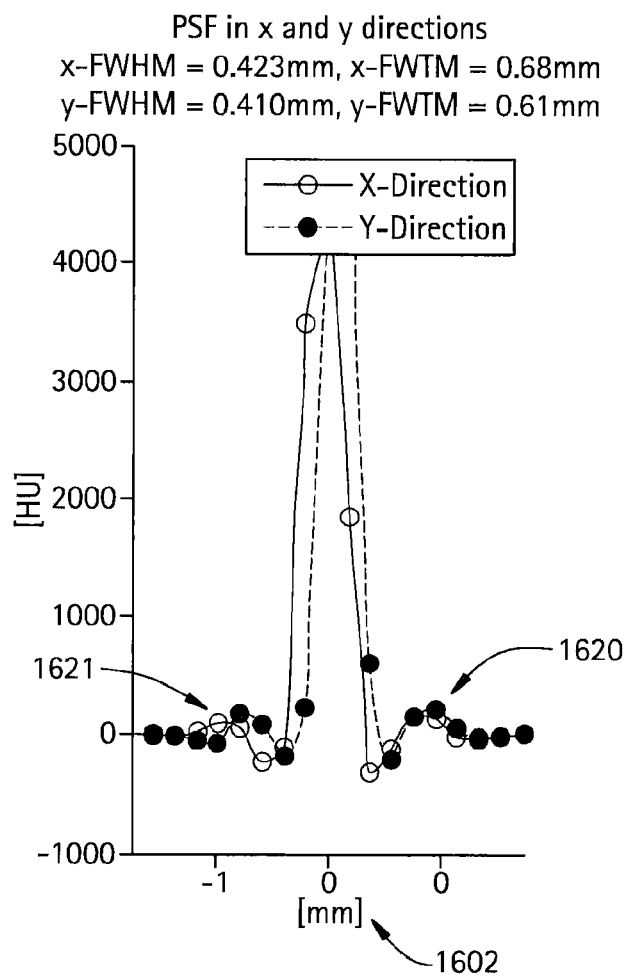
FIG. 16 illustrates a point spread function of the response of an imaging system employing enlarged voxel model iterative reconstruction, according to an example embodiment.
Figure 20:
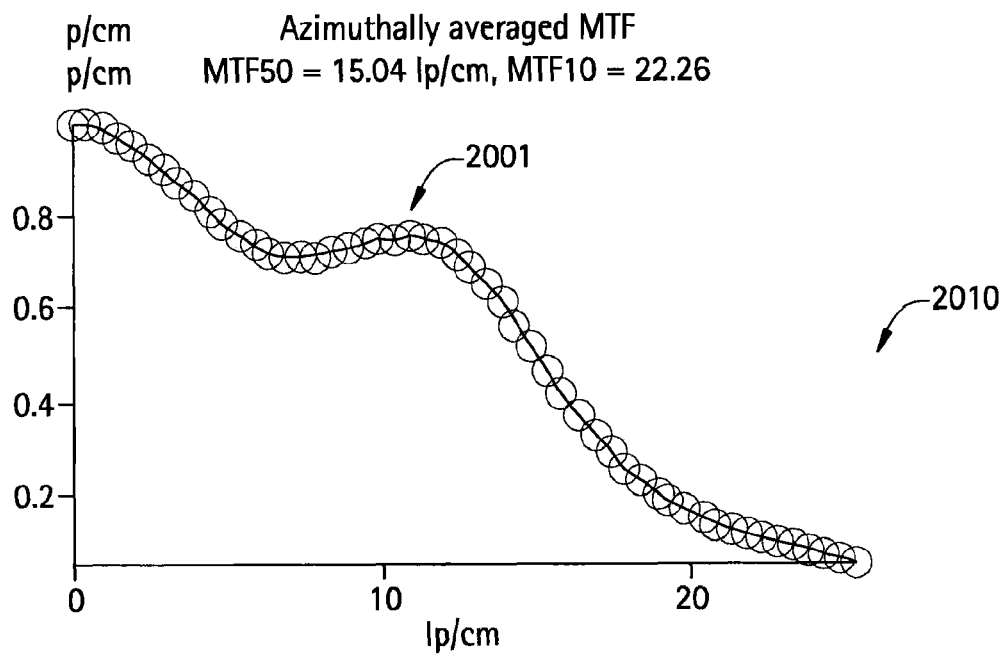
FIG. 20 illustrates an unfiltered modulation transfer function of the response of an imaging system employing enlarged voxel model iterative reconstruction, according to an example embodiment.

FIGS. 15 and 16 illustrate a point spread function of the response of an imaging system, according to an example embodiment. As illustrated the point spread function is represented in both pictorial 1501 and graphical 1602 forms. The function depicts disturbances 1620 and 1621 which result from peaks in a modulated transfer function of the conventional iterative model. The modulated transfer function (MTF) is represented in FIGS. 20-21. As will become readily apparent, if a band suppression filter is applied, the disturbances caused by MTF peaks are reduced or mitigated.

Figure 17:
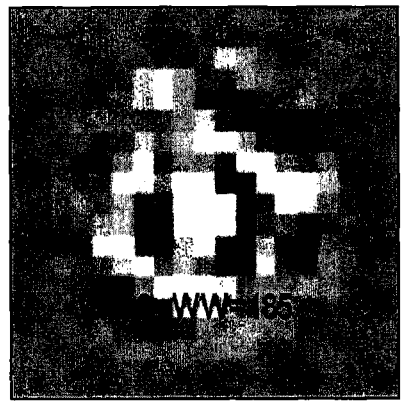
FIG. 17 illustrates a filtered point spread function of the response of an imaging system employing enlarged voxel model iterative reconstruction, according to an example embodiment.
Figure 18:
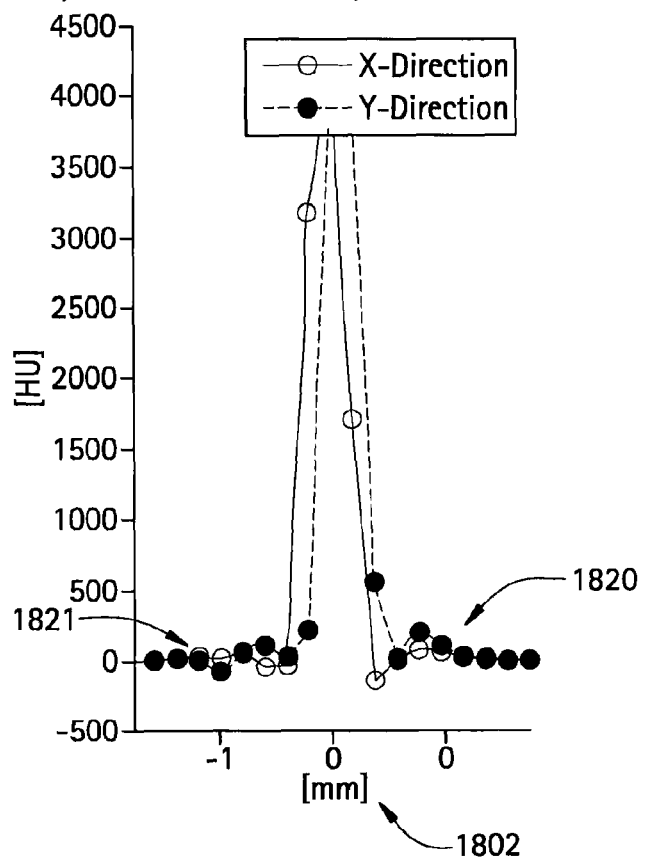
FIG. 18 illustrates a filtered point spread function of the response of an imaging system employing enlarged voxel model iterative reconstruction, according to an example embodiment.

FIGS. 17 and 18 illustrate a filtered point spread function of the response of an imaging system, according to an example embodiment. As illustrated the point spread function is represented in both pictorial 1701 and graphical 1802 forms. The function depicts reduced disturbances 1820 and 1821 which result from a reduction in the peaks of a modulated transfer function of the exemplary iterative model. The modulated transfer function (MTF) is represented in FIGS. 20-21. As is apparent, if a band suppression filter is applied, the disturbances caused by MTF peaks are reduced or mitigated.

Figure 19:
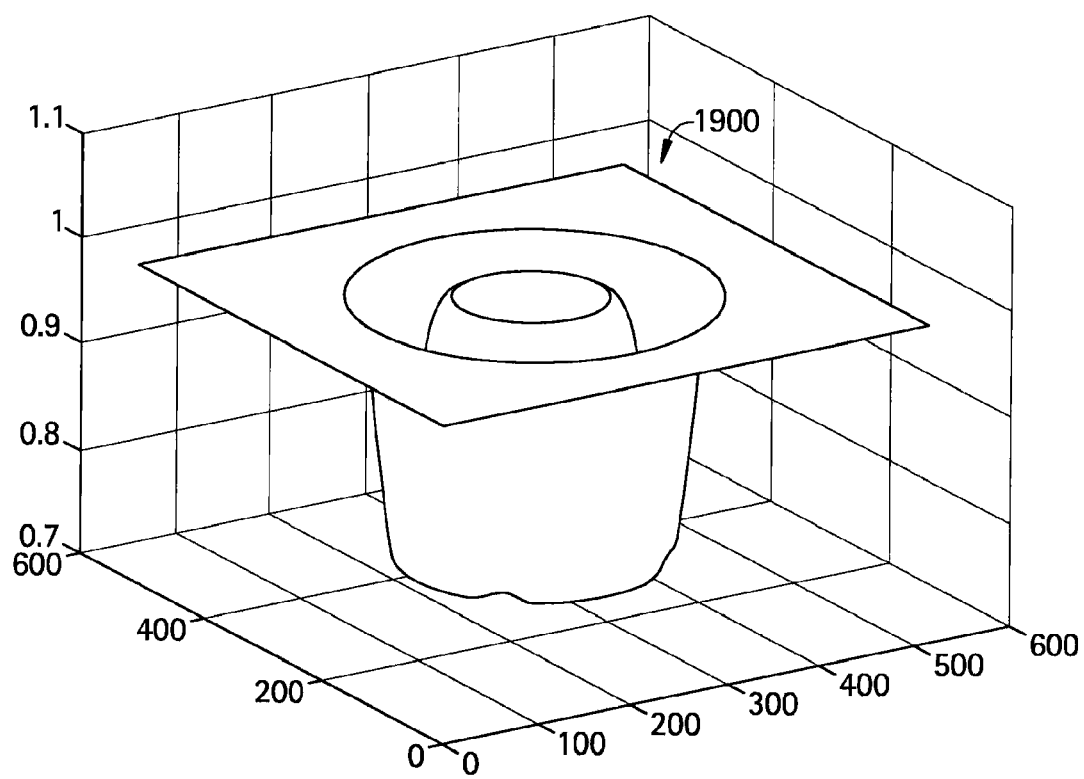
FIG. 19 illustrates a band-suppression filter model, according to an example embodiment.

FIG. 19 illustrates an example of a band-suppression filter model as applied to FIGS. 17-18, according to an example embodiment. As illustrated, the band-suppression characteristics of the filter 1900 reduce the disturbances illustrated in FIGS. 15-16. The band-suppression filter 1900 may be implemented by taking a Fourier transform (FFT) (in the image or projection domain), attenuating the frequencies that correspond to the over-/under-shoot artifacts resulting from enlarged/voxels/detectors, and taking the inverse Fourier transform (IFFT).

FIGS. 20-21 illustrate filtered and unfiltered modulation transfer functions of the response of an imaging system, according to an example embodiment. The unfiltered MTF of graph 2010 includes a peak 2001 which is analog to the disturbances pointed out in FIGS. 15-16. However, as band suppression filter 1900 is applied, the post-filtration graph 2120 depicts a reduction or mitigation of the peak as outlined in area 2102 of the graph 2120.

Hereinafter, a more detailed description of methodologies of iterative reconstruction are provided. As noted above, traditional reconstruction approaches, including FBP-type approaches, typically assume point voxels, a point source, and point detectors. Interpolation is performed to project or backproject the values corresponding to these points. Iterative reconstruction approaches often model the source as a point, the detectors as points, and the voxels as points. However, some methods have been published that take into account the finite extent of source, voxels and detectors.

The voxel size may be chosen to be equal to the spacing between two voxels, and the detector size may be chosen to be equal to the spacing between two cells, or less, to model the active area. In contrast, according to example embodiments, methods including enlarged voxel and/or the detector models are provided. For example, the models used in defining the iterative reconstruction algorithm includes a voxel/detector size that is larger than the inter-voxel/inter-detector distance. Thus, example embodiments may overcome the drawbacks of the traditional point source, voxel, and detector models.

Figure 22:
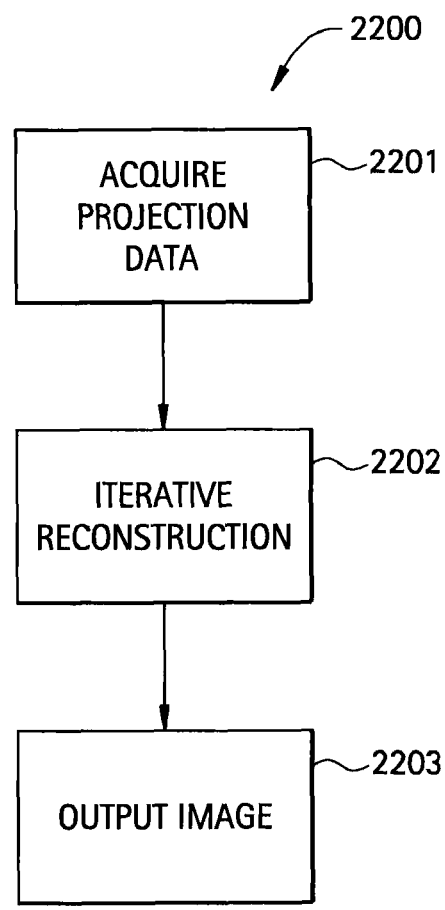
FIG. 22 is a flowchart of a method of iterative reconstruction, according to an example embodiment.

FIG. 22 is a flowchart of a method of iterative reconstruction, according to an example embodiment. The method 2200 includes an exemplary optimization iterative reconstruction method. The method 2200 begins by acquiring projection data received by a detector array (see FIGS. 1-6) at block 2201. The projection data is then processed in iterative reconstruction process at block 2202 before the high quality reconstruction image is output at block 2203.

The iterative reconstruction process of block 2202 may include any proposed enhancement outlined herein. According to at least one example embodiment, the iterative reconstruction process includes voxel/detector boosting through enlarging voxels, detectors, or any combination thereof. For example, FIGS. 5-6 illustrate enlarged voxel/detector implementations. Furthermore, the iterative reconstruction may include, in addition to enlarged voxel/detector models, an iterative reconstruction forward model as described above with reference to FIG. 9. Additionally, cost function minimization in iterative image reconstruction may also be included, and is discussed more fully in co-pending U.S. patent application Ser. No. 12/199,833 entitled "METHOD AND SYSTEM FOR IMAGE RECONSTRUCTION" which is hereby incorporated by reference in its entirety.

However, example embodiments are not limited to iterative reconstruction methods comprising only enlarged voxel/detector sizes. For example, a plurality of different artifact reduction methodologies may be used in combination therewith. Possible additional artifact reduction techniques are described more fully with reference to FIG. 23.

FIG. 23 is a flowchart of a method of improved iterative reconstruction, according to an example embodiment. The method 2300 includes acquiring projection data at block 2301. The projection data may be acquired from an imaging system as described in FIGS. 1-6.

Upon acquisition, the method 2300 includes processing the projection data in iterative reconstruction process at block 2302 before the high quality reconstruction image is output at block 2303.

The iterative reconstruction process may include a plurality of additional sub-processes configured to enhance the output image and/or reduce artifacts. It is noted however, that although block 2302 is illustrated including all of the below-described enhancements, any one or more enhancement may be omitted in any particular implementation. Therefore, example embodiments should not be limited to the particular combination illustrated, but rather should be defined by the appended claims.

According to at least one example embodiment, the iterative reconstruction includes enlarging voxels/detectors at block 2321. The voxel/detector enlargement may be similar to the enlargement described above with reference to FIGS. 3-6.

According to at least one example embodiment, the iterative reconstruction includes implementing a trapezoidal footprint at block 2322 for one or both of the voxels and detectors. For example, trapezoidal footprint implementation is described more fully above with reference to FIGS. 9-10.

According to at least one example embodiment, the iterative reconstruction includes implementing a neighborhood-dependent non-constant voxel model (NDNC) at block 2324.

For example, a NDNC model can be used to reduce the aliasing artifacts in high-resolution images caused by jagged edges of simply enlarged voxel models, which may be assumed to be uniform across their entire volume. The NDNC voxel technique can be implemented by computing a slope, which depends on the neighboring voxels, and results in a corresponding slope in the projected voxel footprint. The slope model can be extended to a non-linearly varying voxel model, such as a higher order model. Unlike blobs (e.g., "blob-like" voxels) these models model the variation within the original voxel footprint based on information from neighborhood voxels. The neighborhood of the prior voxel can be adapted to operate on the edge values of the sloped voxel, for example the prior will prefer the right-most value of a given voxel to be close to the left-most value its right neighbor. Alternatively, the voxel is sub-divided into 2 sub-voxels (left-right or up-down) or 4 sub-voxels (4 quadrants) (generally N sub-voxels). The density of each of the sub-voxels is calculated by interpolation with neighborhood voxels on the fly. In a forward projection portion of the iterative reconstruction, the effective voxel footprint is calculated by the sum of all sub-voxels. This may avoid storage of a larger image matrix, as would be the case when reconstructing using smaller voxels. Additionally, as there may be increased overlap in the computation for the N different sub-voxels, the total arithmetic cost may be much less than N times longer. Moreover, those sub-voxels may be limited to some regions, for example strong gradients regions, which will further decrease the computational overhead. The slope and sub-voxel models may be applied in x, y, or z axis or any combination thereof.

According to at least one example embodiment, the iterative reconstruction may include implementation of a non-uniform voxel size model at block 2325.

In contrast to NDNC, which retains voxel size, another technique to achieve modeling around high frequency regions is to use a smaller voxel size near those high frequency regions, with larger voxel sizes in other regions, thereby including non-uniform voxel sizes across different regions. However, the non-uniform voxel size model may require more memory to store more voxels, and a more complex implementation keeping track of the multi-resolution image description (i.e., the voxel size changes as a function of location and anatomical content). Conventional methods utilize smaller voxels for an entire image space. However, the high frequency components discussed above may be limited to edges or high-contrast regions. Therefore, enhanced results may be achieved by applying smaller voxels for only edge regions or high-frequency regions. Thus, the proposed non-uniform voxel size model implemented at edge-regions can keep the additional computation cost at a relatively low level.

According to at least one example embodiment, the iterative reconstruction may include adaptive regularization of the iterative reconstruction at block 2326.

For example, in a case of quadratic priors within the projection data, spatial resolution may suffer because of the smoothing effect of the prior. Typically, edge-preserving priors are used to achieve a better trade-off between noise reduction and spatial resolution. Example embodiments may be configured to adjust the prior parameters (any of them, but the prior strength and weights in particular) based on a gradient map or edge map. For example, a quadratic prior can be used with reduced strength near edges in order to preserve spatial resolution. In addition example embodiments may change the prior weights directionally based on the direction of the gradient to achieve more isotropic resolution.

According to at least one example embodiment, the iterative reconstruction may include general sinogram pre-processing at block 2327.

For example, any technique used for filtered back-projection in terms of filter or preprocessing on sinogram may be adapted to iterative reconstruction. For example, in high-resolution mode (e.g., focal spot deflection mode), the projection data is interleaved and processed by a filter to enhance resolution (similarly to FBP but without the ideal ramp filter), then the preprocessed data are used in iterative reconstruction. With the aid of a pre-processing filter, a resolution boost may be achieved by iterative reconstruction. Beside those filtration operations, better physics modeling of the imaging system may be included into the pre-processing, such as deconvolution of the imaging beam source blurring effect, modeling of the electronic noise in the sinogram data, beam hardening correction, scatter correction, and other suitable operations. Hence, a more accurate sinogram representation can be achieved with more accurate physics model, leading to improved image quality of the output image.

According to at least one example embodiment, the iterative reconstruction may include iterative reconstruction for general focal spot wobbling geometry.

Focal spot wobbling at the imaging beam source level increases the sampling rate of the CT scanner and therefore helps achieve higher spatial resolution. Unlike the "interleaved" technique discussed above used by filtered backprojection, the wobbled views may be kept apart and the true wobbled focal spot positions may be incorporated in the IR forward model. Incorporating a correct forward model can enhance resolution, minimize noise and avoid artifacts. This may be particularly useful if the focal spot positions are sub-optimal for interlacing. Further, more complex physical processes, such as the finite time it takes for the focal spot to move, focal spot size modulation, mA modulation, kVp modulation, various imaging beam filters, bowtie, may also be modeled if necessary.

Additionally, according to at least one example embodiment, the iterative reconstruction includes implementing a band-suppression filter at block 2323 after iterative reconstruction. For example, the band suppression filter may be somewhat similar to the band suppression filter 1900 of FIG. 19. Finally, the method 2300 includes outputting the reconstructed image at block 2303.

As described above, improvements to iterative reconstruction in imaging systems are provided. The improvements may be based on increased or enlarged voxel/detector sizes in acquired projection data, and may be used with a combination of other resolution enhancing techniques as outlined above.

Example embodiments of the present invention improve the spatial resolution of iterative reconstruction, reduce or eliminate the aliasing artifacts in output images particularly in low contrast structures, and reduce or eliminate over- and under-shoot artifacts that may result from artificially boosting resolution.

Thus example embodiments of the present invention provide enhancements to iterative reconstruction that improve reconstruction in line with results from conventional reconstruction techniques including FBP with finely tuned filtration kernels that help achieve high spatial resolution. Additionally, the proposed resolution boosting techniques induce limited impact on the reconstruction performance (i.e., speed). For example, voxel/detector enlargement and other enhancements are faster than techniques that directly model the physical blurring process. Additionally, the reduction in aliasing artifacts improves iteratively reconstructed images, especially for low contrast structures. Without using the proposed techniques, streak artifacts tend to appear especially when the regularization is reduced to achieve higher resolution (see FIG. 10). Furthermore, as compared with blob modeling methods, which also try to mimic artificially larger voxel profiles in the forward model, example embodiments are simpler (e.g., only a linear profile is used), resulting in better reconstruction performance. For example, the NDNC voxel model addition, which only requires more computation around edge pixels, may reach the same artifacts level as images reconstructed with two-times smaller pixels. Furthermore, example embodiments reduce over- and under-shoot artifacts which improves images around edges, such as skin and bone. Additionally, the modified voxel/detector system model works efficiently in currently available framework, which makes it inexpensive to integrate it into new iterative reconstruction methods.

An embodiment of the invention may be embodied in the form of computer-implemented processes and apparatuses for practicing those processes. The present invention may also be embodied in the form of a computer program product having computer program code containing instructions embodied in tangible media, such as floppy diskettes, CD-ROMs, hard drives, USB (universal serial bus) drives, or any other computer readable storage medium, such as random access memory (RAM), read only memory (ROM), or erasable programmable read only memory (EPROM), for example, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to reconstruct two dimensional projection data into three dimensional image data that may be used by a clinician for diagnostic purposes.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. An improved iterative reconstruction method to reconstruct a first image, the method comprising:
   generating an imaging beam;
   receiving said imaging beam on a detector array;

generating projection data based on said imaging beams received by said detector array;
providing said projection data to an image reconstructor;
enlarging one of a plurality of voxels and a plurality of detectors of the provided projection data, wherein enlarging the plurality of voxels comprises modeling the plurality of voxels with an overlap between neighboring voxels, and wherein enlarging the plurality of detectors comprises modeling the plurality of detectors with an overlap between neighboring detectors;
iteratively reconstructing portions of the first image with the plurality of enlarged voxels or detectors to create a reconstructed image;
implementing non-uniform voxel sizes for the plurality of voxels; and
implementing neighborhood dependent non-constant (NDNC) voxels for the non-uniform voxels.

2. The method of claim 1, further comprising outputting the iteratively reconstructed first image; and
wherein enlarging the plurality of detectors comprises modeling the plurality of detectors with a detector aperture larger than a physical aperture of the plurality of detectors.

3. The method of claim 1, further comprising applying a band suppression model to the reconstructed image.

4. The method of claim 1, further comprising generating trapezoidal footprints for the plurality of enlarged voxels or detectors.

5. The method of claim 4, wherein the trapezoidal footprints are generated such that overlap of the plurality of enlarged voxels or detectors is linear and minimizes peaks within a forward projection model of the plurality of enlarged voxels or detectors.

6. The method of claim 1, wherein the non-uniform voxels include smaller voxels near high-frequency regions of the projection data.

7. The method of claim 1, wherein the non-uniform voxels include smaller voxels at edge regions of an object represented within the projection data.

8. The method of claim 1, wherein the NDNC voxels include projected slopes of neighboring voxels on respective footprints of the plurality of voxels.

9. The method of claim 8, wherein the projected slopes are calculated simultaneous to implementing the non-uniform voxels.

10. The method of claim 8, wherein the projected slopes are only calculated for voxels at edge regions of an object represented within the projection data, or the projected slopes are only calculated for voxels near high-frequency regions of the projection data.

11. The method of claim 8, wherein the projected slopes are calculated to project from the right-most value of a first voxel to the left-most value of a right neighbor of the first voxel.

12. The method of claim 1, wherein the NDNC models include divisions of voxels of the plurality of voxels into sub-voxels, each sub-voxel having a density based upon interpolation of densities of neighboring voxels.

13. The method of claim 12, wherein the densities of sub-voxels are calculated simultaneous to sub-voxel creation.

14. The method of claim 12, wherein the sub-voxels are created only for voxels near high-frequency regions of the projection data or for voxels near edge regions of an object represented within the projection data.

15. The method of claim 1, further comprising wobbling a focal spot of the imaging beam.

16. The method of claim 1, further comprising sinogram pre-processing of the provided projection data, wherein the pre-processed projection data is used for voxel or detector model enlargement.

17. An imaging system comprising:
a source constructed to project an imaging beam toward an object;
a detector array positioned to receive said imaging beam and generate projection data;
a translatable table configured for disposal of said object thereon; and
an image reconstructor electrically coupled to said detector array, said image reconstructor having a processor programmed to:
generate an enlarged voxel/detector model to represent a plurality of voxels and a plurality of detectors of the projection data, wherein the enlarged voxel/detector model defines an overlap between at least one of adjacent voxels and adjacent detectors;
iteratively reconstruct portions of the first image using the enlarged voxel/detector model to create a reconstructed image;
implement non-uniform voxels for the plurality of voxels, wherein the non-uniform voxels include smaller voxels near high-frequency regions of the projection data or at edge regions of an object represented within the projection data; and
implement neighborhood dependent non-constant (NDNC) voxels for the non-uniform voxels, wherein the NDNC voxels include projected slopes of neighboring voxels on respective footprints of the plurality of voxels.

18. The imaging system of claim 17, wherein the processor is further programmed to apply a band suppression model to the reconstructed image.

19. The imaging system of claim 17, wherein the processor is further programmed to generate trapezoidal footprints for the plurality of enlarged voxels or detectors; and
wherein the trapezoidal footprints are generated such that overlap of the plurality of enlarged voxels or detectors is linear and minimizes peaks within a forward projection model of the plurality of enlarged voxels or detectors.

20. The imaging system of claim 17, wherein the processor is further programmed to:
either only calculate projected slopes for voxels at edge regions of an object represented within the projection data; or
only calculate the projected slopes for voxels near high-frequency regions of the projection data.

21. The imaging system of claim 17, wherein the processor is further programmed to implement neighborhood dependent non-constant (NDNC) voxels for the non-uniform voxels; and
wherein the NDNC voxels include divisions of voxels of the plurality of voxels into sub-voxels, each sub-voxel having a density based upon interpolation of densities of neighboring voxels.

22. An improved iterative reconstruction method to reconstruct a first image, the method comprising:
generating an imaging beam;
receiving said imaging beam on a detector array;
generating projection data based on said imaging beams received by said detector array;
providing said projection data to an image reconstructor;
neighborhood dependent non-constant (NDNC) voxels for a plurality of voxels of the provided projection data;

reconstructing portions of the first image with the plurality of NDNC voxels; and iteratively reconstructing the portions of the first image to create a reconstructed image.

23. The method of claim 22, wherein the NDNC voxels include projected slopes of neighboring voxels on respective footprints of the plurality of voxels.

24. The method of claim 23, wherein the projected slopes are calculated simultaneous to implementing the NDNC voxels.

25. The method of claim 23, wherein the projected slopes are only calculated for voxels at edge regions of an object represented within the projection data, or the projected slopes are only calculated for voxels near high-frequency regions of the projection data.

26. The method of claim 23, wherein the projected slopes of a first voxel are estimated from the right-most value of left neighbor of the first voxel to the left-most value of a right neighbor of the first voxel.

27. The method of claim 22, wherein the NDNC models include divisions of voxels of the plurality of voxels into sub-voxels, each sub-voxel having a density based upon interpolation of densities of neighboring voxels.

28. The method of claim 27, wherein the densities of sub-voxels are calculated simultaneous to sub-voxel creation.

29. The method of claim 27, wherein the sub-voxels are created only for voxels near high-frequency regions of the projection data or for voxels near edge regions of an object represented within the projection data.

30. The method of claim 23, wherein the projected slopes of a first voxel are estimated from the averaged value of left neighbor of the first voxel to the averaged value of a right neighbor of the first voxel.

31. The method of claim 1, further comprising modeling the plurality of detectors with a footprint geometrically dissimilar to an actual physical shape of the plurality of detectors.

32. The method of claim 1, wherein enlarging the plurality of voxels comprises modeling the plurality of voxels with a voxel size larger than a physical distance between neighboring voxels; and wherein enlarging the plurality of detectors comprises modeling the plurality of detectors with a detector size larger than a physical distance between neighboring detectors.

* * * * *